(12) United States Patent
Jung et al.

(10) Patent No.: US 8,933,017 B2
(45) Date of Patent: Jan. 13, 2015

(54) CD44V6 PEPTIDES AS INHIBITORS OF BACTERIAL INFECTIONS

(71) Applicant: Karlsruher Institut fur Technologie, Karlsruhe (DE)

(72) Inventors: Christian Jung, Karlsruhe (DE); Véronique Orian-Rousseau, Rittershofen (FR); Alexandra Matzke, Pforzheim (DE); Helmut Ponta, Weingarten (AT)

(73) Assignee: Karlsruher Institut fur Technologie, Karlsruhe (DE)

( * ) Notice: Subject to any disclaimer, the term of this patent is extended or adjusted under 35 U.S.C. 154(b) by 67 days.

(21) Appl. No.: 13/673,749

(22) Filed: Nov. 9, 2012

(65) Prior Publication Data
US 2013/0072423 A1 Mar. 21, 2013

Related U.S. Application Data

(62) Division of application No. 12/658,949, filed on Feb. 16, 2010, now abandoned.

(30) Foreign Application Priority Data

Feb. 16, 2009 (EP) .................................... 09002149

(51) Int. Cl.
| | |
|---|---|
| *A61K 38/12* | (2006.01) |
| *A61K 38/10* | (2006.01) |
| *A61K 38/04* | (2006.01) |
| *A61K 38/08* | (2006.01) |
| *C07K 7/08* | (2006.01) |
| *C07K 7/00* | (2006.01) |
| *C07K 5/12* | (2006.01) |
| *A61K 38/17* | (2006.01) |
| *C07K 14/705* | (2006.01) |

(52) U.S. Cl.
CPC ............... *A61K 38/178* (2013.01); *A61K 38/12* (2013.01); *C07K 14/70585* (2013.01)
USPC ............. 514/2.4; 514/2.8; 514/2.9; 514/21.5; 530/317; 530/327

(58) Field of Classification Search
CPC ..... A61K 38/12; A61K 38/178; A61K 38/10; A61K 38/04; A61K 38/08; C07K 7/08; C07K 7/00; C07K 5/12; C07K 14/70585
USPC ............. 514/2.4, 2.8, 2.9, 21.5; 530/317, 327
See application file for complete search history.

(56) References Cited

FOREIGN PATENT DOCUMENTS

| EP | 1647556 | 4/2006 |
|---|---|---|
| WO | WO 00/06738 | 2/2000 |
| WO | WO 2004/092209 A3 | 10/2004 |
| WO | WO 2009/016515 | 2/2009 |

OTHER PUBLICATIONS van 't Hof W, Veerman ECI, Helmerhorst DJ, Amerongen AVN, "Antimicrobial Peptides: Properties and Applicability," Biol. Chem., Apr. 2001, 382(4): 597-619.*
Screaton, GR, Bell MV, Jackson DG, Cornelis FB, Gerth U, Bell JI, "Genomic structure of DNA encoding the lymphocyte homing receptor CD44 reveals at least 12 alternatively spliced exons," Proc. Natl. Acad. Sci, USA, 1992, 89: 12160-12164.*
P16070 from GenBank, earlist sequencing data: 1989, pp. 1-20. Accessed Mar. 10, 2014.*
European Search Report issued for European Application No. 09002149.4-2107 dated Jul. 31, 2009.
Jung, C. et al., Involvement of CD44v6 in InIB-dependent *Listeria* invasion, Molecular Microbiology, 2009, vol. 7(5), pp. 1196-1207.
Definition of derivative and analog from http://cancerweb.ncl.ac.uk/omd/about.html, pp. 1-5. Accessed Jul. 7, 2005.
Rudinger J, "Characteristics of the amino acids as components of a peptide hormone sequence," Peptide Hormones, JA Parsons Edition, University Park Press, Jun. 1976, pp. 1-7.
"Designing Custom Peptides," from SIGMA Genosys, pp. 1-2. Accessed Dec. 16, 2004.
Schinzel R, Drueckes P, "The phosphate recognition site of *Escherichia coli* maltodextrin phosphorylase," FEBS, Jul. 1991, 296 (1, 2): 125-128.
Berendsen HJC, "A Glimpse of the Holy Grail?" Science, 1998, 282:642-643.
Voet D, Voet JG, Biochemistry, Second Edition, John Wiley & Sons, Inc., 1995, pp. 235-241.
Ngo JT, Marks J, Karplus M., "Computational Complexity, Protein Structure Prediction, and the Levinthal Paradox," The Protein Folding Problem and Tertiary Structure Prediction, K. Merc Jr. And S. Le Grand Edition, 1994, pp. 491-495.
Bradley CM, Barrick D, "Limits of Cooperativity in a Structurally Modular Protein: Response of the Notch Ankyrin Doman to Analogous Alanine Substitutions in Each Repeat, "J.Mol.Biol., 2002, 324, 373-386.
Carrolo Margarida et al: "Hepatocyte growth factor and its receptor are required for malaria infection." Nature Medicine, vol. 9, No. 11, Nov. 2003, pp. 1363-1369.
Leiriao, et al.: "HGF/MET signalling protects Plasmodium-infected host cells from apoptosis." Cellular Microbiology vol. 7, No. 4, 2005, pp. 603-609.

* cited by examiner

*Primary Examiner* — Julie Ha
(74) *Attorney, Agent, or Firm* — Knobbe, Martens, Olson & Bear, LLP

(57) ABSTRACT

A method for treatment of infection with *Listeria* spp., *Plasmodium* spp., or *Shigella* spp. includes administering a peptide or a pharmaceutically acceptable salt of the peptide to an individual in need of treatment for the infection.

8 Claims, 5 Drawing Sheets

CD44V6 PEPTIDES AS INHIBITORS OF BACTERIAL INFECTIONS

Figure 1:
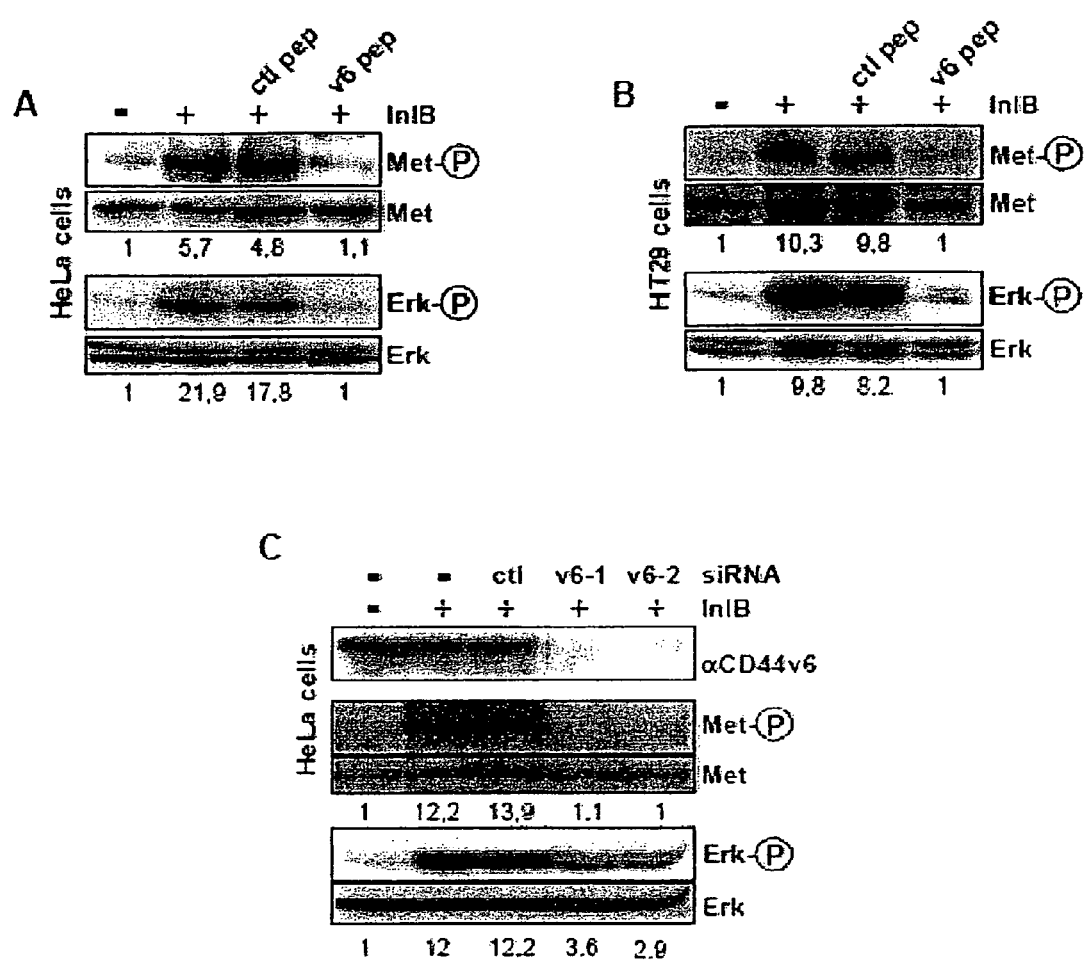

This application is a divisional application of U.S. patent application Ser. No. 12/658,949, filed Feb. 16, 2010 which claims the benefit of European Patent Application No. 09002149.4-2107, filed Feb. 16, 2009. This application incorporates herein by reference U.S. patent application Ser. No. 12/658,949 and European Patent Application No. 09002149.4-2107 in their entirety.

The present invention relates to the use of peptide compounds for the prevention and/or treatment of a bacterial infection.

Bacteria have developed ingenious strategies to invade mammalian cells and to spread from one cell to another. They express proteins that mimic functions of cellular proteins in order to target host cells and promote their entry. One such bacterium is *Listeria monocytogenes*, a food-borne pathogen that can cause listeriosis. This disease manifests as meningitis, encephalitis, gastroenteritis and mother-to-fetus infections that lead to abortion in pregnant women. *L. monocytogenes* induces its uptake into non-phagocytic host cells using surface proteins of the internalin family. Although *L. monocytogenes* expresses several internalins, only two members, internalin A and B (InlA, InlB), are well characterized. InlA is covalently linked to the bacterial cell wall and binds to E-cadherin. InlB is non-covalently bound to bacterial lipoteichoic acids and stimulates c-Met phosphorylation. Both InlA and InlB can independently mediate *L. monocytogenes* invasion. After the initial binding to the cell surface, the bacterium is engulfed by a "zipper" mechanism. Activation of cell surface proteins leads to actin remodeling and membrane extensions so that the bacteria can be driven into the cells. The vacuoles containing the bacteria are then lysed by listeriolysin O, a molecule that can lyse phagosomal membranes. The bacteria are released into the cytoplasm and move from one cell to another using the actin cytoskeleton.

InlB activates c-Met similarly to HGF, the classical c-Met ligand, and induces downstream signaling pathways such as the MAPK or the JNK pathway. Activated c-Met is internalized, a process that normally regulates receptor tyrosine kinase (RTK) activation and turnover. Indeed, shortly after activation by their ligands, RTKs like c-Met are endocytosed, in most cases through a clathrin-dependent mechanism. This internalization process is subverted by *L. monocytogenes* to invade eukaryotic cells.

InlB and HGF do not compete with each other for binding to c-Met. These data speak for the presence of different binding sites for InlB and HGF on c-Met and are consistent with the fact that InlB and HGF have no sequence homology and are not structurally related. InlB consists of several domains including an N-terminal leucine rich repeat (LRR), an Inter-repeat region (IR) followed by a B-repeat (BR) and three C-terminal glycine/tryptophan-rich (GW) domains. The LRR domain is critical for binding to c-Met and is essential for the invasion of bacteria. Four amino acids located in the exposed concave region of the LRR domain seem to be critical for this binding, since mutations of all four amino acids lead to a dramatic decrease of *L. monocytogenes* invasion. The functions of the IR and of the B domains are not well characterized whereas the role of the GW-rich modules seems to be the ability to bind to heparan-sulfate proteoglycans (HSPG). The binding to HSPGs enhances bacterial entry and is critical for c-Met clustering and activation. Also heparin, a sulphated glycosaminoglycan present on HSPGs, induces oligomerization of c-Met. A truncated form of InlB, InlB321 where the B-repeat and GW domains are removed and that cannot bind to heparin, induces phosphorylation of c-Met, but not the phenotypic cellular response like cell scattering or proliferation. This monomeric mutant is unable to dimerize the isolated ligand-binding domain of c-Met in vitro, even in the presence of heparin. Interestingly, in the case of HGF, heparan sulfation is not required for activation of the c-Met receptor. Indeed, a mutant of HGF deficient in heparin sulfate binding is even more potent for c-Met activation than wild type HGF. Furthermore, removal of heparan sulfate moieties from cell surface molecules does not interfere with the activation of c-Met.

CD44 forms a family of transmembrane glycoproteins that play important roles in many cellular processes amongst which are the regulation of growth, survival, differentiation and migration. The smallest isoform is called CD44s or CD44 standard. Larger isoforms differ thereof mainly in their extracellular domain in which inclusion of ten so-called "variant exons" in various combinations can take place. Herein, the term CD44v6 designates isoforms that contain the v6 variant exon either alone or in combination with other variant exons. All CD44v6 isoforms are able to act as a co-receptor for c-Met. In pathological situations, these isoforms confer metastatic propensity to several tumor cells.

The role of CD44v6 for c-Met activation is two-fold: the extracellular part of CD44 is needed for activation of the receptor itself whereas the cytoplasmic tail is instrumental for signaling. The cytoplasmic domain of CD44v6 recruits the actin cytoskeleton via binding to ERM (Ezrin-Radixin-Moesin) proteins. CD44v6, HGF, c-Met, ERM proteins together with the cytoskeleton form a signalosome complex that promotes signaling. For instance, Ras activation by its guanine-nucleotide exchange factor SOS did not occur in cells transfected with a mutant form of CD44v6 where the cytoplasmic domain had been removed. Furthermore, siRNA repressing ezrin abrogated HGF induced signaling to Erk. Finally, an ezrin protein that lacked the actin-binding domain (ezΔABD) acted in a dominant negative fashion and repressed the activation of Erk induced by HGF.

The co-receptor function of CD44v6 for c-Met is not unique. For instance, VEGFR-2 that plays a pivotal role in angiogenesis also requires CD44v6 for activation and for signaling. Interestingly, the same CD44v6 peptides that block c-Met activation also inhibited the activation of VEGFR-2 induced with VEGFA-165 and reveal a role of CD44 in angiogenesis. More and more evidence shows that several RTK-ligand units recruit other players such as cell adhesion molecules most likely to fine-tune the signaling events. Examples are FGFRs or EGFRs that recruit members of the syndecan and cadherin family as co-receptors.

Therefore, one technical problem underlying the present invention is to provide a medicament that can inhibit bacterial infection.

The solution to the above technical problem is achieved by the embodiments characterized in the claims.

In particular, the present invention relates to a peptide compound comprising an amino acid sequence displayed by amino acids 7 to 11 of SEQ ID NO: 2 or of SEQ ID NO: 1, or a functionally active derivative thereof, or a pharmaceutically acceptable salt thereof, for use in the prevention and/or treatment of a bacterial infection in an individual.

In another aspect, the present invention relates to a peptide compound comprising an amino acid sequence displayed by SEQ ID NO: 2 or SEQ ID NO: 1, or a functionally active derivative thereof, or a pharmaceutically acceptable salt thereof, for use in the manufacture of a medicament for the prevention and/or treatment of a bacterial infection in an individual.

In a preferred embodiment, the peptide compound of the present invention is a peptide consisting of amino acids 7 to 11 of SEQ ID NO: 2 or of SEQ ID NO: 1. In another preferred embodiment of the present invention, the peptide compound of the present invention is a peptide comprising or consisting of SEQ ID NO: 2 or SEQ ID NO. 1.

The peptide compound of the present invention may be any peptide compound described in European patent application EP 1 647 556 which is hereby incorporated by reference in its entirety.

In a preferred embodiment, the peptide compound of the present invention comprises or consists of a fragment of SEQ ID NO: 2 or of SEQ ID NO: 1, said fragment having the activity of inhibiting the complex formation between CD44, c-Met and InI-B leading to the phosphorylation and internalization of c-Met, as well as to phosphorylation of Erk.

For example the peptide compound of the present invention is selected from the group consisting of peptides comprising or consisting of the amino acid sequence as shown in SEQ ID NO: 2 or SEQ ID NO: 1;

peptides consisting of a fragment of SEQ ID NO: 4 or of SEQ ID NO: 3, and having the activity of inhibiting the complex formation between CD44, c-Met and InIB leading to the phosphorylization and internalization of c-Met, as well as to phosphorylation of Erk;

heterologous fusion peptides comprising or consisting of a peptide according to (a) or (b) fused to a heterologous amino acid sequence; and derivatives of a peptide according to (a), (b) or (c) having the activity of inhibiting the complex formation between CD44, c-Met and InIB leading to the phosphorylization and internalization of c-Met, as well as to phosphorylation of Erk.

In a preferred embodiment of the present invention, the peptide compound of the present invention is selected from the group consisting of peptides comprising or consisting of the amino acid sequence as shown in SEQ ID NO: 2 or SEQ ID NO: 1, peptides comprising or consisting of any one of the following amino acid sequences:
amino acids 2 to 14 of SEQ ID NO: 2 or 1,
amino acids 2 to 13 of SEQ ID NO: 2 or 1,
amino acids 2 to 12 of SEQ ID NO: 2 or 1,
amino acids 2 to 11 of SEQ ID NO: 2 or 1,
amino acids 3 to 14 of SEQ ID NO: 2 or 1,
amino acids 3 to 13 of SEQ ID NO: 2 or 1,
amino acids 3 to 12 of SEQ ID NO: 2 or 1,
amino acids 3 to 11 of SEQ ID NO: 2 or 1,
amino acids 4 to 14 of SEQ ID NO: 2 or 1,
amino acids 4 to 13 of SEQ ID NO: 2 or 1,
amino acids 4 to 12 of SEQ ID NO: 2 or 1,
amino acids 4 to 11 of SEQ ID NO: 2 or 1,
amino acids 5 to 14 of SEQ ID NO: 2 or 1,
amino acids 5 to 13 of SEQ ID NO: 2 or 1,
amino acids 5 to 12 of SEQ ID NO: 2 or 1,
amino acids 5 to 11 of SEQ ID NO: 2 or 1,
amino acids 6 to 14 of SEQ ID NO: 2 or 1,
amino acids 6 to 13 of SEQ ID NO: 2 or 1,
amino acids 6 to 12 of SEQ ID NO: 2 or 1,
amino acids 6 to 11 of SEQ ID NO: 2 or 1,
amino acids 7 to 14 of SEQ ID NO: 2 or 1,
amino acids 7 to 13 of SEQ ID NO: 2 or 1,
amino acids 7 to 12 of SEQ ID NO: 2 or 1,
amino acids 7 to 11 of SEQ ID NO: 2 or 1,
and heterologous fusion peptides comprising (a) or (b) fused to a heterologous amino acid sequence.

The peptide compound of the present invention may comprise amino acid sequences derived from other proteins. Therefore, in a preferred embodiment, the peptide compound of the present invention comprises fusion peptides comprising one of the above amino acid sequences fused to a another, preferably heterologous, amino acid sequence. The heterologous amino acid sequence may comprise or consist of 1, 2, 3, 4 or more amino acids. The heterologous amino acid sequence may for example comprise or consist of at least 5 or at least 10 or at least 20 heterologous amino acids. The heterologous amino acid sequences may be fused to the N- and/or C-terminus of the peptide compound of the present invention.

In a further embodiment of the present invention, the peptide compound of the present invention is a derivative of the peptides described above. The term "derivative" as used herein comprises functionally active derivatives, variants and chemical derivatives of the peptide compound.

The term "functionally active derivative" as used herein related to derivatives which contain deletions, additions and/or substitutions of amino acids, the presence, absence or substitution of which does not have a substantial influence on the activity of the peptide compound, e.g. conservative amino acid substitutions, i.e. substitution of an amino acid by an amino acid having similar chemical properties. The term "derivative" includes post-translational modifications, e.g. glycosylation patterns that differ from the wild-type.

A "variant" of a peptide is meant to refer to a molecule substantially similar to either the entire peptide, or a fragment thereof having essentially the same function. A variant of a first peptide may be a second peptide which has 1 to 5, preferably 1 to 4, more preferably 1 to 3, more preferably 1 or 2 amino acid substitutions, additions and/or deletions with respect to said first peptide. For example, variants of SEQ ID NO: 2 may have 1 to 5 amino acid substitutions with respect to SEQ ID NO: 2, as long as the activity of inhibiting the complex formation between CD44, c-Met and InI-B leading to the phosphorylation and internalization of c-Met, as well as to phosphorylation of Erk, is substantially the same as that of the peptide consisting of the amino acid sequence as shown in SEQ ID NO: 2.

A molecule is a "chemical derivative" of a first peptide when it contains additional chemical moieties not present in the first peptide. Such moieties may improve for example the molecule's solubility, absorption, or biological half-life. The moieties may alternatively for example decrease the toxicity of the molecule, or eliminate or attenuate any undesirable side effect of the molecule.

Generally, the derivative has at least 75%, preferably at least 100% of the activity of inhibiting the complex formation between CD44, c-Met and InI-B leading to the phosphorylation and internalization of c-Met, as well as to phosphorylation of Erk of the peptide compound from which it is derived.

The term "fragment" of a given peptide as used herein is meant to refer to any peptide subset of said peptide. Generally, a fragment comprises at least 2 contiguous amino acids of the sequence of said peptide. Preferably, the fragment comprises at least 4, more preferably at least 5, more preferably at least 6, more preferably at least 8, even more preferably at least 10 contiguous amino acids of said peptide.

Methods for determining the activity of inhibiting the complex formation between CD44, c-Met and InI-B leading to the phosphorylation and internalization of c-Met, as well as to phosphorylation of Erk are well known in the art. The peptide compound of the invention has the activity of inhibiting the complex formation between CD44, c-Met and InI-B leading to the phosphorylation and internalization of c-Met, as well as to phosphorylation of Erk, measured in form of the activation of the Erk protein through phosphorylation. The inhibitory activity results in a reduction of downstream Erk activation. Preferably, downstream Erk activation is reduced by at least 30%, more preferably by at least 50% and even more preferably by at least 70% with respect to the downstream Erk activation in the presence of a control peptide. For example the activity can be determined in cell culture.

The term "peptide compound" as used herein denotes a compound comprising at lease one peptide. In one embodiment of the present application the "peptide compound" consists of a peptide. The term "peptide compound" includes compounds comprising a peptide and a chemical moiety which is not an amino acid.

The term "peptide" as used herein refers to any compound comprising two or more amino acids joined to each other by peptide bonds or modified peptide bonds, i.e. peptide isosteres. "Peptide" refers to both short chains and to longer chains, generally referred to as polypeptides. Peptides may contain amino acids other than the 20 gene-encoded amino acids. Peptides include amino acid sequences modified either by natural processes, such as post-translational processing, or by chemical modification techniques which are well known in the art. Modifications can occur anywhere in a peptide, including the peptide backbone, the amino acid side-chains and the amino or carboxyl termini. The same type of modification may be present in the same or varying degrees at several sites in a given peptide. Also, a given peptide may contain many types of modifications.

Peptides may be branched and they may be cyclic, with or without branching. Cyclic, branched and branched cyclic peptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, ubiquitination and sumoylation.

The term "peptide compound" may as a preferred embodiment include salts, preferably pharmaceutically acceptable salts of the peptides described herein. Salts encompassed within the term "pharmaceutically acceptable salts" refer to non-toxic salts of the peptide compounds of this invention. Representative salts and esters include the following: acetate, ascorbate, benzenesulfonate, benzoate, bicarbonate, bisulfate, bitartrate, borate, caamsylate, carbonate, citrate, dihydrochloride, methanesulfonate, ethanesulfonate, p-toluenesulfonate, cyclohexylsulfamate, quinate, edetate, edisylate, estolate, esylate, fumarate, gluconate, glutamate, glycerophophates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate. Other salts include Ca, Li, Mg, Na, and K salts; salts of amino acids such as lysine or arginine; guanidine, diethanolamine or choline; ammonium, substituted ammonium salts or aluminum salts. The salts are prepared by conventional methods.

The peptide of the invention has a length of at least 2 amino acids. Preferably, the length of the peptide is at least 4, more preferably at least 5, more preferably at least 6, more preferably at least 8, most preferably at least 10 amino acids. The maximum length is not particularly limited. It is preferred, however, that the peptide has a length of from about 6 to about 30 amino acids, preferably of from about 8 to about 25 amino acids, more preferably of from about 10 to about 20 amino acids, most preferably of from about 10 to about 15 amino acids. Larger peptides may be employed, for example when fusion peptides with heterologous amino acid sequences are prepared.

It is preferred that the peptide of the present invention is an isolated peptide.

It is also preferred that the peptide of the present invention is in a pure state. Preferably, the peptide is 80% pure, preferably 90% pure, more preferably 95% pure, even more preferably 99% pure and particularly preferred is a pharmaceutically pure state that is greater than 99.9% pure with respect to contaminating macromolecules, particularly other peptides. It is preferred that the peptide is free of infectious and pyrogenic agents.

Preferably, a purified peptide is substantially free of other peptides. When used in this context, the term "pure" does not exclude the presence of the same peptide in alternative physical forms, such as dimers.

The peptides of the present invention may be prepared by chemical synthesis or by recombinant expression in host cells. The preparation by chemical synthesis is preferred. As protein products, compounds of SEQ ID NO: 2 or 1 or other peptides of the present invention are amenable to production by the technique of solution- or solid-phase peptide synthesis. The synthetic peptide synthesis approach generally entails the use of automated synthesizers and appropriate resins as solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and trifluoroacetic acid as ion-pairing agent. Such procedures are generally described in numerous publications.

The peptide compound of the present invention may be a chemically derived structure, diverted from the peptide sequences described herein, or a pharmaceutically acceptable salt and/or physiologically functional derivative thereof. The chemically derived structure can be a cyclopeptide or a pharmaceutically acceptable salt and/or physiologically functional derivative thereof. The invention further includes the use of a substance metabolized to a peptide compound of the invention.

The individual according to the present invention may be any individual which is susceptible to a bacterial infection. In a preferred embodiment the individual is a vertebrate, more preferably a mammal, like for example a mouse, a rat, a human, a rabbit, a pig a cattle, or a horse, and most preferably a rat or a human.

In a preferred embodiment of the present invention, the bacterial infection is an infection with an intracellular bacterium. Preferably, the intracellular bacterium is selected from the group consisting of *Listeria* spp., *Mycobacterium* spp., *Plasmodium* spp., and *Shigella* spp. An especially preferred intracellular bacterium is *Listeria monocytogenes*.

In a preferred embodiment of the present invention, the intracellular bacterium is a bacterium, wherein the cellular uptake of the bacterium is mediated by InIB-induced activation of c-Met.

In a preferred embodiment of the present invention, the intracellular bacterium is a bacterium, wherein the cellular uptake of the bacterium involves the formation of a complex between CD44, c-Met and InIB, leading to the phosphorylation and internalization of c-Met, as well as to phosphorylation of Erk.

In yet another preferred embodiment of the present invention, the bacterial infection is listeriosis.

The medicament of the present invention can be formulated as e.g., liquids, suspensions, emulsions, lozenges, cachets, ampoules, suppositories, pessaries, ointments, gels, pastes, sprays, lotions, oils, boluses, electuaries, aerosols, powders, granules, tablets, pills, capsules, injections, solutions, foams, creams, enemas and the like, comprising at least one compound of the present invention alone or in admixture with pharmaceutically acceptable carriers, excipients and/or diluents.

Specific dose levels of the medicament of the present invention for any particular patient will be employed depending upon a variety of factors including the age, body weight, general health, sex, diet, and prior medication, and the severity of the particular disease of the patient, and the activity of specific compounds employed, time of administration, route of administration, rate of excretion, the duration of the treatment, other drugs, compounds, and/or materials used in combination. The appropriate dosage of medicament can vary from patient to patient. Determining the optimal dosage will generally involve balancing of the level of therapeutic benefit against any risk or deleterious side effects of the treatment.

Administration in vivo can be effected in one dose, continuously or intermittently throughout the course of treatment. Methods of determining the most effective means and dosages of administration are well known to those of skill in the art, and will vary with the formulation used for therapy, the purpose of the therapy, the target cell being treated, and the subject being treated. Single or multiple administrations can be carried out with the dose level and pattern being selected by the treating physician.

In general, a suitable systemic dose of the active compound of the medicament of the present invention is in the range of about 0.01 to about 1000 mg per kilogram body weight preferably 0.1 to 500 mg per kilogram body weight and even more preferably 1.0 to 500 mg per kilogram body weight of the subject per day. Where the active ingredient is a salt, an ester, prodrug, or the like, the amount administered is calculated on the basis of the parent compound and so the actual weight to be used is increased proportionately. In case the compound is applied locally, the amount of compound may vary from the above given estimation. However, such an application would aim at reaching local concentrations of the drug ranging from about 0.1 ng/ml to 10 mg/ml, more preferred from 1 ng/ml to 1 mg/ml.

The figures show:

FIG. 1: InIB Requires CD44v6 for c-Met Activation

HeLa cells were induced with InIB (A) at a concentration of 1 nM for 5 min at 37° C. Pretreatment with a control peptide or a CD44v6 14-mer peptide having SEQ ID NO: 2 at a concentration of 100 ng/ml for 30 min was performed when indicated. Phosphorylation of c-Met and of Erk were measured as described in experimental procedures. The same experiments were performed with the HT29 cells (B). (C) HeLa cells were transfected with two different siRNA (v6-1 and v6-2, described in experimental procedures) to downregulate CD44v6 and with a control siRNA. 48 h after transfection, cells were starved for additional 24 h. InIB-induced c-Met and Erk phosphorylation were measured. The expression of CD44v6 was detected by Western Blot analysis. The numbers reflect-fold induction as determined by densitometric scanning (Image J program).

Figure 2:
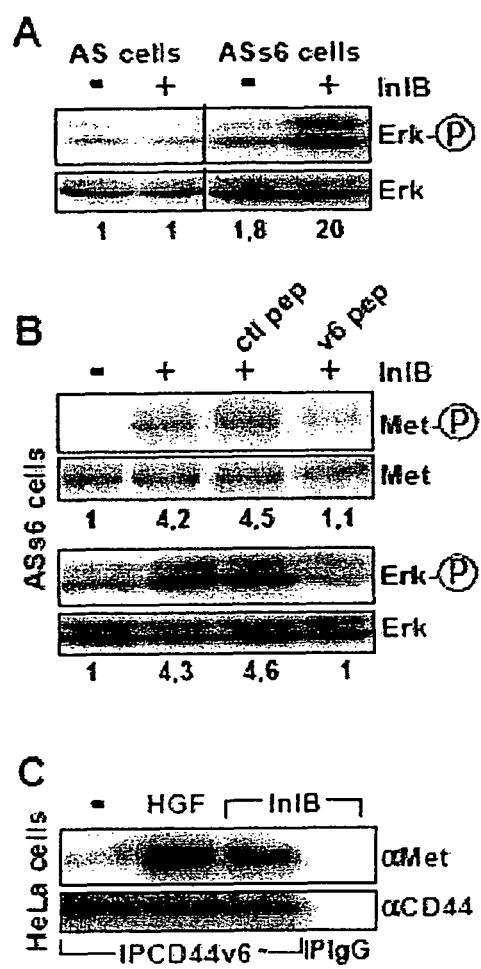

FIG. 2: A CD44v6 Isoform is Sufficient for InIB-Induced c-Met Activation

AS cells or ASs6 cells were induced with InIB as indicated (A) and ASs6 cells in addition with a CD44v6 14-mer peptide having SEQ ID NO: 1 or an unrelated (control) peptide (B). Erk phosphorylation (A,B) or c-Met phosphorylation (B) was determined. In (C), HeLa cells were induced either with HGF or InIB for 5 min at 37° C. CD44v6 was immunoprecipitated from the lysates and a Western Blot was performed using CD44v6 and c-Met antibodies as indicated. For control, an IgG antibody was used. The numbers reflect-fold induction as determined by densitometric scanning (Image J program).

Figure 3:
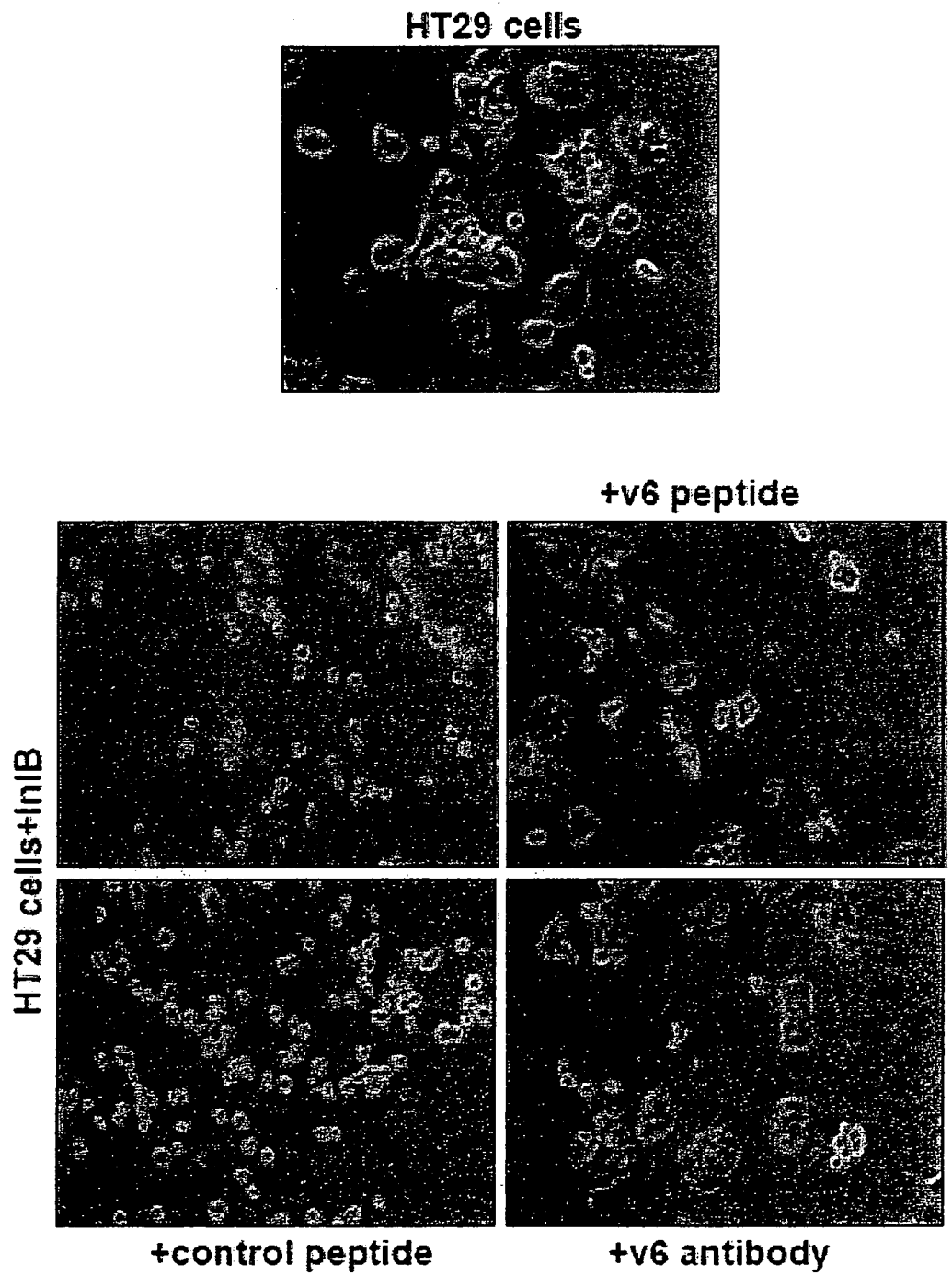

FIG. 3: InIB-Induced Scattering is Blocked by a CD44v6 Peptide

Scattering of HT29 cells was determined after treatment with InIB alone or together with a control peptide or a CD44v6 peptide or antibody as indicated. The magnification used was ×20.

Figure 4:
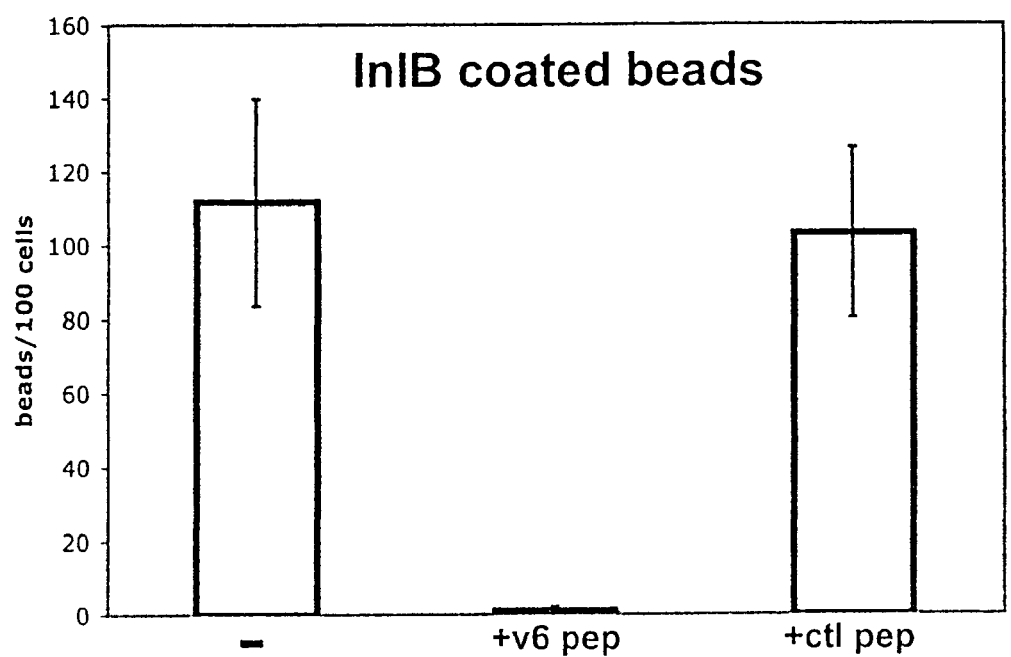

FIG. 4: Uptake of InIB-Coated Latex Beads is Dependent on CD44v6

Control beads or beads coated with InIB (see experimental procedures) were incubated with HeLa cells. Cells were pretreated with a CD44v6 peptide having SEQ ID NO: 2 or a control peptide for one hour as indicated. Extracellular beads bind to a Cy3-labelled antibody and are stained red in immunofluorescence microscopy. In phase contrast microscopy both extracellular and intracellular beads are detected. The number of internalized beads (black) was counted in approximately a thousand cells and shown as intracellular beads/100 cells in the graph. The results are expressed as means±standard deviation of three independent experiments.

Figure 5:
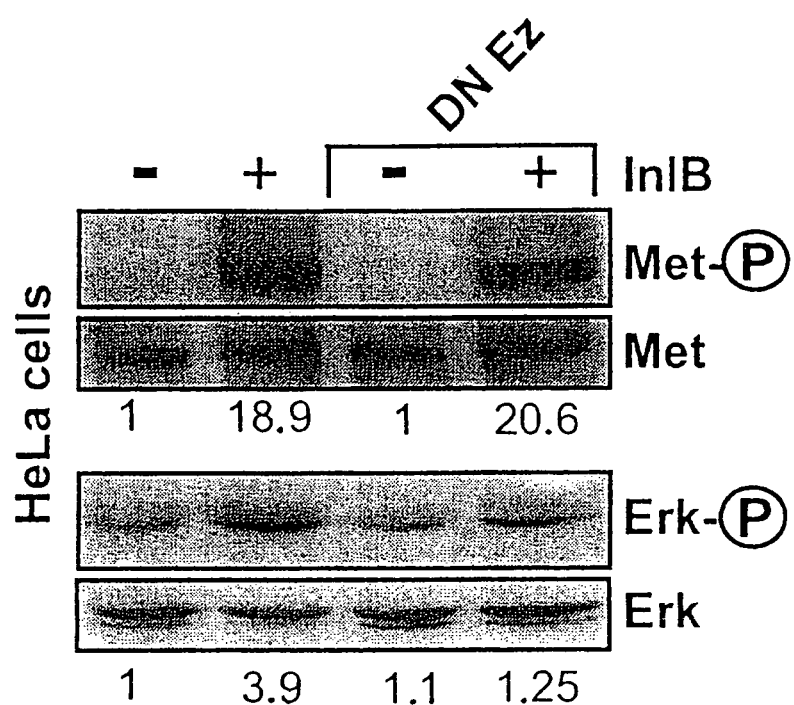

FIG. 5: Ezrin-Dependent Uptake of InIB-Coated Beads.

In1B-dependent c-Met and Erk phosphorylation was measured in HeLa cells transiently transfected with a control vector or a vector coding for a truncated version of ezrin deprived of the actin binding domain (ezΔABD or DN Ezrin). In these cells also the uptake of latex beads was determined as described in FIG. 4. The counts of internalized beads obtained for three independent experiments are given in Table 1.

The present invention will now be further illustrated in the following examples without being limited thereto.

EXAMPLES

Experimental Procedures

Cells.

The human colon adenocarcinoma cell lines HT29 and the human cervix carcinoma cell line HeLa (American tissue culture collection, ATCC; Wesel, Germany. Accession no: CCL-2) were grown in Dulbecco's modified Eagle's medium (DMEM; Invitrogen, Karlsruhe, Germany) supplemented with 10% fetal calf serum (FCS; PAA Cölbe, Germany). The rat pancreatic carcinoma cell line BSp73AS and its transfectant BSp73ASs6 were grown in RMPI (Invitrogen, Karlsruhe, Germany) plus 10% FCS.

Antibodies and Other Reagents.

The human monoclonal antibody against CD44v6 (Biwa) was obtained from Bender (Vienna, Austria). The pan-CD44 antibody IM7 was from Pharmingen, the antibody against Erk 1 (K-23) from Santa Cruz (Calif., USA). The Phospho-Erk antibody (Phospho-p44/42 Map Kinase) was purchased from Cell Signalling Technology (Beverly, England). Secondary antibodies labeled with HRP were purchased from Dako (Hamburg, Germany). Mouse IgG was obtained from Santa Cruz (Calif., U.S.A). The hybridoma cell supernatant of anti-InlB monoclonal antibody was a kind gift from J. Wehland, Braunschweig, Germany. HGF was a generous gift of George Vande Woude (Van Andel Institute, USA). InlB was prepared as is known in the art. The CD44 v6 peptide (14-mer: KEQW-FGNRWHEGYR, SEQ ID NO:2) and the control peptide were synthesized by NMI Technology Transfer (Reutlingen, Germany). An ezrin construct where the last 29 amino acids encoding the actin-binding domain have been deleted has been kindly provided by Monique Arpin (CNRS, Paris, France). The Cy-3 labeled secondary antibody was bought from Dianova (Hamburg, Germany).

Detection of c-Met and Erk Phosphorylation.

In all experiments cells were induced with 1 nM of InlB where indicated. Induction was performed for 5 min at 37° C. Blocking experiments were performed by incubating the CD44v6 14-mer peptide having for example SEQ ID NO: 2 or SEQ ID NO: 1 (100 ng/ml) or the control peptide (100 ng/ml) for 30 min at 37° C. prior to induction with InlB. Cells were lysed with sample buffer+DTT and subjected to SDS-PAGE. The corresponding blots were treated with the respective antibodies according to the manufacturer instructions.

Co-Immunoprecipitation.

HT29 cells were induced with InlB (1 nM) or with HGF (0.15 nM) for 5 min at 37° C. Cells were lysed using a buffer containing 25 mM Hepes pH 7.5; 100 mM NaCl; 10 mM $MgCl_2$; 1 mM EDTA; 10% Glycerol; 1% NP40. Lysates were cleared by centrifugation at 15000 rpm for 30 min. Cleared lysates were incubated with an anti-CD44v6 antibody (IM7) over night followed by an incubation with a mixture of Protein A and Protein G agarose beads (Pierce, Rockford, USA) for 2 h. The beads were washed 3 times with the lysis buffer and solubilized in sample buffer+DTT. The samples were loaded on an SDSPAGE gel and blotted with the anti-phospho-Met antibody.

Scattering Assay.

HT29 cells were seeded at a concentration of $3 \times 10^5$ cells/well in a 6-well plate. They were then incubated with InlB (1 nM) for 48 h at 37° C. For the blocking experiments, CD44 anti-v6 antibodies (Biwa; 100 μg/ml) or a CD44v6 peptide (100 ng/ml) were added before addition of InlB. Pictures were taken using a phase contrast microscope 48 h after induction.

siRNA Inhibition.

Cells were transfected with CD44v6 specific siRNAs (eurofins MWG GmbH, Ebersberg, Germany):

(Quiagen, Hilden, Germany, Cat. No. 1022076) using lipofectamine 2000 (Invitrogen, Karlsruhe, Germany) according to the manufacturer's protocol. 48 h post-transfection the cells were starved for 24 h and then treated with InlB as described above.

Latex Bead Invasion Assay.

Coating of the beads with InlB was performed as is known in the art. Briefly, 25 μl of latex beads ($4 \times 10^8$ beads/ml, Dynabeads M-450, Dynal, Invitrogen, Karlsruhe, Germany) were coated with goat anti-mouse IgG and then incubated with 0.5 ml of hybridoma cell supernatant of monoclonal anti-InlB antibody for 2 h at 4° C. After washing with PBS, the beads were incubated with InlB (3 μM) latex beads coated with both the goat anti-mouse IgG and the anti-InlB mAb were used as control beads. For the invasion assay, $2 \times 10^4$ cells were seeded in chamber slides (LabTek Chamber slides, Nunc, Langenselbold, Germany). Cells were incubated for 2 h with the InlB-coated beads or control beads in 0.2 ml of complete DMEM at 37° C. The cells were washed with 0.5 ml of medium and incubated in medium for 1 h at 37° C. After this incubation time, the cells were washed three times with 1 ml of CB buffer (10 mM Pipes, 150 mM NaCl, 5 mM EGTA, 5 mM glucose, 5 mM MgCl2, 100 μg/ml streptomycin), fixed with 4% paraformaldehyde in CB buffer for 30 min and washed with PBS. The non-permeabilized cells were incubated with 0.2 ml of BSA (1% in CB buffer and incubated with a Cy3-labeled goat anti-mouse antibody (1:200 dilution) to detect the extracellular beads. Intracellular and extracellular beads were detected by phase contrast microscopy. An overlay of fluorescence scans and bright field scans show the internalized beads in black and the extracellular beads in red. Cells were mounted in PVA and viewed using microscope (Axioskop 200M (fluo), Zeiss, Jena, Germany). Intracellular beads were counted in approximately 1000 cells. Each experiment was repeated at least three times and results were analyzed statistically.

Example 1

InlB Requires CD44v6 for c-Met Activation

CD44v6 is necessary for HGF-induced c-Met activation. This was demonstrated by means of CD44v6 specific antibodies, CD44v6 peptides and CD44v6-specific siRNA that all blocked the activation of c-Met. These tools were used to investigate whether CD44v6 also plays a role in InlB-induced activation of c-Met and signaling. In HT29 and in HeLa cells, where a contribution of CD44v6 to HGF-induced c-Met activation was already observed a human CD44v6 14-mer peptide having SEQ ID NO: 2 completely abrogated InlB-induced activation of c-Met (FIG. 1A, B). Also downstream signaling monitored by Erk activation was inhibited. A control peptide had no effect. By means of siRNA against CD44v6, the requirement of CD44v6 was further confirmed.

```
                                                       (SEQ ID NO: 5)
v6-1:         siRNA 25nt 5'-AGU AGU ACA ACG GAA GAA ATT-3'

(SEQ ID NO: 6)
v6-2:         siRNA 25nt 5'-GGA UAU CGC CAA ACA CCC ATT-3' or control    siRNA (AATTCTCCGAACGTGTCACGT, SEQ ID NO: 7)
```

Two different siRNAs down-regulated CD44v6 expression in HeLa cells and thereby inhibited InlB-induced c-Met and Erk activation (FIG. 1C).

Thus, a CD44v6-specific peptide and siRNA against CD44v6 are able to block InlB-induced activation of c-Met and subsequent signaling. The HT29 and HeLa cells used in these experiments express CD44 variant isoforms containing exon v6 together with other variant exons. In order to confirm the dependency of c-Met activation on CD44v6 and to test whether an isoform containing exclusively exon v6 was sufficient for the activation of c-Met, rat pancreatic carcinoma cells (BSp73AS, abbreviated AS, FIG. 2) or these cells transfected with such a CD44v6 isoform (BSp73ASs6, abbreviated ASs6) were used. These cells express this CD44v6 isoform as the only variant isoform in addition to CD44s. In the AS cells, no activation of c-Met was observed after addition of InlB, whereas activation was detected in cells expressing CD44v6 (FIG. 2A). Therefore, this experiment not only confirmed that a CD44v6 isoform is needed for InlB-induced activation but it also demonstrated that exon v6 inclusion alone was sufficient. As expected, InlB-induced c-Met and Erk phosphorylation were abrogated in these ASs6 cells upon treatment with the CD44v6 peptide having SEQ ID NO:1 (FIG. 2B).

Example 2

CD44v6, c-Met and InlB Form a Complex

The results so far suggest that CD44v6, c-Met and InlB are in close vicinity and form a complex. To identify such a complex CD44v6 was immunoprecipitated and the presence of c-Met in the complex checked. Indeed, upon induction with InlB, endogenous c-Met and CD44v6 were co-immunoprecipitated (FIG. 2C), whereas no complex was observed in the absence of InlB. In the control IgG immunoprecipitation, no association between c-Met and CD44v6 is to be observed.

Example 3

CD44v6 Mediates InlB-Induced Scattering and Entry of InlB-Coated Beads

InlB similarly to HGF can induce complex biological responses such as scattering upon activation of c-Met. It was tested whether scattering was also dependent on CD44v6. As expected, both a anti-CD44v6 antibody and a CD44v6-specific peptide having SEQ ID NO: 2 blocked this response (FIG. 3). InlB-activated c-Met is internalized leading to the entry of the bacteria into the host cells. This process can be simulated using InlB-coated latex beads that are also internalized into mammalian cells. The latex beads invasion assay was used to test the effect of a CD44v6 peptide on InlB-induced cellular entry. The beads were first coated with an anti-mouse antibody followed by a monoclonal antibody (mAb) against InlB and then loaded with InlB. HeLa cells were incubated with control beads (only coated with the anti-mouse antibody together with the anti-InlB mAb) or InlB-coated beads. In order to distinguish between beads that have entered the cells and beads that remained outside, a Cy3-labelled antibody directed against the anti-InlB mAb was used. As the cells were not permeabilized, this labeled antibody could only bind to beads that remained outside. The binding of this antibody can be detected by immunofluorescence microscopy. In phase contrast microscopy, however, all beads can be seen. An overlay between the two pictures allows distinguishing between beads in and outside the cells. The red beads are the ones outside the cells whereas the black beads correspond to the internalized ones. Control beads without InlB are all excluded from the cells whereas InlB-coated beads can enter. A drastic decrease of the entry was observed when HeLa cells were preincubated with the CD44v6 peptide. The entry was blocked to nearly 100%. The control peptide had no effect on the uptake. Intracellular beads were counted in approximately one thousand cells (FIG. 4). These data demonstrate that CD44v6 is instrumental for the entry of InlB-coated beads into the cells suggesting that also the entry of the bacteria itself might depend on CD44v6.

Example 4

ERM Proteins are Essential for Entry of InlB-Coated Beads in Cells

The recruitment of ERM proteins together with the cytoskeleton to CD44v6 is a decisive step in c-Met dependent signal transduction. In order to investigate if ERM proteins and the cytoskeleton are also necessary for internalization of In1B-coated beads, an ezrin protein that lacks the actin binding (ezΔABD) ability was used. This protein acts in a dominant negative fashion on signal transduction. In the case of HGF it competes with endogenous ezrin and has a dramatic effect on Erk phosphorylation whereas c-Met activation itself is not affected. The same is true for In1B-induced c-Met and Erk activation (FIG. 5). Transfection of HeLa cells with this dominant negative ezrin construct completely abrogated the entry of In1B-coated beads whereas transfection with a control vector had no effect. The number of internalized beads for approximately one thousand cells was counted and the results of three independent experiments are shown in Table 1. In conclusion, the link of ezrin to the cytoskeleton is instrumental for entry of In1B-coated beads.

TABLE 1

Ezrin is required for entry of InlB-coated beads into cells

| HeLa cells | Experiment 1 | | Experiment 2 | | Experiment 3 | |
| --- | --- | --- | --- | --- | --- | --- |
| | +vector | +DN Ezrin | +vector | +DN Ezrin | +vector | +DN Ezrin |
| InlB beads per 100 cells | 56 | 4 | 81 | 1 | 83 | 1 |

It has been shown that InlB activation of c-Met is dependent on CD44v6. Indeed, InlB-induced c-Met activation as well as downstream Erk phosphorylation can be blocked by means of a CD44v6 peptide and upon downregulation of CD44v6 by siRNA. In addition, induction of c-Met via InlB in a cell line that lacks CD44v6 is possible only after transfection of CD44v6. InlB induces a complex between c-Met and CD44v6 as shown by co-immunoprecipitation. In addition, scattering and in particular, entry of InlB-coated beads that mimic the entry of L. monocytogenes into cells is dependent on CD44v6. This event is also regulated by ezrin binding to the cytoskeleton. Taken together these data demonstrate a role of CD44v6 in InlB-mediated L. monocytogenes invasion of eukaryotic cells.

HGF and InlB share no structural similarities and bind to different sites on c-Met. However, the same CD44v6 peptide blocks activation of c-Met induced by both ligands. A likely explanation would be that the CD44v6 peptide inhibits the interaction between CD44v6 and c-Met and thereby its activation. This however seems not to be the case. The CD44v6 peptide rather addresses CD44v6 itself changing its conformation. This observation could also explain how the same CD44v6 peptide blocks the activation of a completely different receptor, VEGFR-2.

InIB recruits heparin to activate c-Met. CD44v6 does not seem to act itself as an HSPG in the case of InIB induction, as only the CD44v3-containing isoforms can be heparan-sulphated and the HT29 cells do not express the v3 and the v6 exons in the same isoform. Furthermore, it has been shown that an isoform of CD44 containing only the v6 exon was sufficient to support InIB-induced Erk phosphorylation. This isoform can certainly not be heparan-sulphated.

The recruitment of heparin by InIB leads to the clustering of c-Met, a process required for full activation. The activation of the c-Met receptor via InIB is the first step necessary for InIB-mediated *L. monocytogenes* uptake into host cells. The bacteria uptake by means of InIB-coated beads was simulated. Their uptake can be completely inhibited by CD44v6-specific peptides demonstrating that CD44v6 is instrumental for infection of cells by *L. monocytogenes*. Interestingly also *Shigella* makes use of CD44 for its entry into mammalian cells. *Shigella* is responsible for bacillary dysentery in humans. It secretes several proteins named IpaA-D that are essential for the infection process. One of them, IpaB interacts with CD44s. This binding is essential for bacteria invasion.

In the case of InIB, signaling depends on the actin cytoskeleton. Transfection of an ezrin protein lacking the actin-binding domain leads to a drastic reduction of Erk phosphorylation but not of c-Met activation. More strikingly, also the uptake of InIB-coated beads is dependent on ezrin binding to the cytoskeleton. These data fit perfectly with recent evidence showing that actin is necessary for clathrin-dependent internalization since the disruption of actin assembly leads to a complete block of this process. Interestingly, also *Shigella* invasion via CD44 requires ezrin for the entry process.

Taken together, the data shown here demonstrate that a link from c-Met to the cytoskeleton via the CD44v6 cytoplasmic domain and ERM proteins is required for InIB-dependent uptake of beads into cells showing a similar mechanism mediating *L. monocytogenes* invasion of host cells.

What is claimed is:

1. A method for treatment of a bacterial infection in an individual comprising:
    administering to an individual in need of treatment of bacterial infection a peptide compound comprising the amino acid sequence set forth in amino acids 7 to 11 of SEQ ID NO: 2, or a pharmaceutically acceptable salt of said peptide in an amount of about 0.01 to about 1000 mg of per kg body weight of a subject per day throughout a course of treatment effective to treat the bacterial infection,
    wherein the bacterial infection is an infection with an intracellular bacterium selected from the group consisting of *Listeria* spp., *Plasmodium* spp., and *Shigella* spp.

2. The method according to claim 1, wherein the peptide compound comprises SEQ ID NO: 2.

3. The method according to claim 1, wherein the intracellular bacterium is *Listeria monocytogenes*.

4. The method according to claim 2, wherein the bacterial infection is listeriosis.

5. The method according to claim 2, wherein the peptide compound is a cyclopeptide or a pharmaceutically acceptable salt thereof.

6. The method according to claim 1, wherein the intracellular bacterium is *Listeria monocytogenes*.

7. The method according to claim 1, wherein the bacterial infection is listeriosis.

8. The method according to claim 1, wherein the peptide compound is a cyclopeptide or a pharmaceutically acceptable salt thereof.

* * * * *

SEQUENCE LISTING

```
<160> NUMBER OF SEQ ID NOS: 7

<210> SEQ ID NO 1
<211> LENGTH: 14
<212> TYPE: PRT
<213> ORGANISM: Rattus norvegicus

<400> SEQUENCE: 1

Lys Glu Lys Trp Phe Glu Asn Glu Trp Gln Gly Lys Asn Pro
1               5                   10

<210> SEQ ID NO 2
<211> LENGTH: 14
<212> TYPE: PRT
<213> ORGANISM: Homo sapiens

<400> SEQUENCE: 2

Lys Glu Gln Trp Phe Gly Asn Arg Trp His Glu Gly Tyr Arg
1               5                   10

<210> SEQ ID NO 3
<211> LENGTH: 42
<212> TYPE: PRT
<213> ORGANISM: Rattus norvegicus

<400> SEQUENCE: 3

Trp Ala Asp Pro Asn Ser Thr Thr Glu Glu Ala Ala Thr Gln Lys Glu
1               5                   10                  15

Lys Trp Phe Glu Asn Glu Trp Gln Gly Lys Asn Pro Pro Thr Pro Ser
            20                  25                  30

Glu Asp Ser His Val Thr Glu Gly Thr Thr
        35                  40

<210> SEQ ID NO 4
<211> LENGTH: 42
<212> TYPE: PRT
<213> ORGANISM: Homo sapiens

<400> SEQUENCE: 4

Gln Ala Thr Pro Ser Ser Thr Thr Glu Glu Thr Ala Thr Gln Lys Glu
1               5                   10                  15
```

```
Gln Trp Phe Gly Asn Arg Trp His Glu Gly Tyr Arg Gln Thr Pro Arg
            20                  25                  30

Glu Asp Ser His Ser Thr Thr Gly Thr Ala
        35                  40

<210> SEQ ID NO 5
<211> LENGTH: 21
<212> TYPE: DNA
<213> ORGANISM: artificial
<220> FEATURE:
<223> OTHER INFORMATION: siRNA molecule

<400> SEQUENCE: 5
aguaguacaa cggaagaaat t                                              21

<210> SEQ ID NO 6
<211> LENGTH: 21
<212> TYPE: DNA
<213> ORGANISM: artificial
<220> FEATURE:
<223> OTHER INFORMATION: siRNA molecule

<400> SEQUENCE: 6
ggauaucgcc aaacacccat t                                              21

<210> SEQ ID NO 7
<211> LENGTH: 21
<212> TYPE: DNA
<213> ORGANISM: artificial
<220> FEATURE:
<223> OTHER INFORMATION: siRNA molecule

<400> SEQUENCE: 7
aattctccga acgtgtcacg t                                              21
```